United States Patent
Farrell et al.

(10) Patent No.: US 7,232,797 B2
(45) Date of Patent: Jun. 19, 2007

(54) ERYTHROPOIETIN DOSING REGIMEN FOR TREATING ANEMIA

(75) Inventors: Francis Farrell, Doylestown, PA (US); Linda K. Jolliffe, Hillsborough, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/304,382

(22) Filed: Nov. 26, 2002

(65) Prior Publication Data

US 2003/0134795 A1  Jul. 17, 2003

Related U.S. Application Data

(60) Provisional application No. 60/333,958, filed on Nov. 28, 2001.

(51) Int. Cl.
*A61K 38/00* (2006.01)
*C07K 14/00* (2006.01)
*C07K 14/505* (2006.01)

(52) U.S. Cl. .............................. 514/2; 514/814; 514/8; 530/350

(58) Field of Classification Search ................... 514/8, 514/814, 2; 530/350
See application file for complete search history.

(56) References Cited

U.S. PATENT DOCUMENTS

| 5,643,575 A | 7/1997 | Martinez et al. ......... 424/194.1 |
| 5,688,679 A | 11/1997 | Powell ..................... 435/240.2 |

FOREIGN PATENT DOCUMENTS

| EP | 0 640 619 A1 | 3/1995 |
| WO | WO 94/12650 | 6/1994 |
| WO | WO 98/05363 | 2/1998 |
| WO | WO 99/05268 | 2/1999 |
| WO | WO 99/11781 | 3/1999 |
| WO | WO 99/38890 | 8/1999 |
| WO | WO 99/66054 | 12/1999 |
| WO | WO 00/67776 | 11/2000 |

OTHER PUBLICATIONS

Farrell et al. Administration of epoetin alfa every two weeks is able to sustain target hemoglobin in a nonhuman primate alternate dosing model. Nov. 16, 2001, Blood, vol. 98, No. 11, Part 1, pp. 297a).*
Piccoli et al. A Decision Analysis Comparing Three Dosage Regimens of Subcutaneous Epoetin in Continous Ambulatory Peritoneal Dialysis. 1995, PharmacoEconomics, vol. 7, No. 5, pp. 444-456.*
Nomoto et al. A Multicenter Study with Once a Week or Once Every Two Weeks High-Dose Subcutaneous Administration of Recombinant Human Erythyropoietin in Continuous Ambulatory Peritoneal Dialysis, 1994, Pert. Dial. Int. vol. 14, pp. 56-60.*
Weiss, Lars. Flexible dosing schemes for recombinant human erythropoietin—Lessons from our daily practice. Jul. 2001, Nephrol. Dial. Transplant. 16 [Supp. 7], pp. 15-19.*
Piccoli et al. Subcutaneous epoetin-alpha every one, two, and three weeks in renal anemia. 2002, J. Nephrol. vol. 15, No. 5, p. 565-574.*
Wognum, A.W. Mini-Review: Erythropoietin, Stemcell Technologies, pp. 1-4, 29013, Version 1.0.0, found at www.stemcell.com/technical/29013_epo.pdf.*
Lundin, A.P., et al., "Exercise in hemodialysis patients after treatment with recombinant human erythropoietin," *Nephron*, 1991, 58, 315-319.
Silverberg, D.S., et al., "The use of subcutaneous erythropoietin and intravenous iron for the treatment of the anemia of severe, resistant congestive heart failure improves cardiac and renal function and functional cardiac class, and markedly reduces hospitalizations," *J. of the American College of Cardiology*, 2000, 35(7), 1737-1744.
Breymann C, et al. "Optimal Timing of Repeated Rh-erythropoietin Administration Improves its Effectiveness in Stimulating Erythropoiesis in Healthy Volunteers", *Brit J Heamatol*. 1996, 92:295-301.
Egrie JC., "Characterization and Biological Effects of Recombinant Human Erythropoietin", *Immunobiology*, 1986, 172, 213-224.
Faulds D., "Epoetin (Recombinant Human Erythropoietin): A Review of its Pharmacodynamic and Pharmacokinetic Properties and Therapeutic Potential in Anemia and the Stimulation of Erythropoiesis", *Drugs*, 1989, 38:863-899.
Jacobs K., et al. "Isolation and Characterization of Genomic and cDNA Clones of Human Erythropoietin", *Nature*, 1985, 313:806-810.
Jelkmann W., "Erythropoietin: Structure, Control of Production, and Function", *Physiol Rev*, 1992, 72(2), 449-489.
Koury ST,. et al., "Localization of Erythropoietin Synthesizing Cells in Murine Kidneys by in Situ Hybridization", *Blood*, 1988, 71(2), 524-527.
Lin FK, et al., Cloning and Expression of the Human Erythropoietin Gene. *Proc Natl Acad Sci*, USA, 1985 82:7580-7584.
Markham A, Bryson HM., "Epoetin Alfa: A Review of its Pharmacodynamic and Pharmacokinetic Properties and Therapeutic Use in Nonrenal Applications", *Drugs*, 1995 49(2), 232-254.

* cited by examiner

*Primary Examiner*—Nashaat T. Nashed
*Assistant Examiner*—Holly G. Schnizer
(74) *Attorney, Agent, or Firm*—Yunling Ren

(57) ABSTRACT

The present invention provides a new subcutaneous injection dosing regimen for erythropoietin to treat anemia. The new erythropoietin treatment regimen of the present invention results in improved hemoglobin levels with less frequent dosing.

10 Claims, 5 Drawing Sheets

ERYTHROPOIETIN DOSING REGIMEN FOR TREATING ANEMIA

CROSS REFERENCE TO RELATED APPLICATIONS

This application claims priority of the benefits of the filing of provisional U.S. application Ser. No. 60/333,958, filed Nov. 28, 2001. The complete disclosures of the aforementioned related U.S. patent application is hereby incorporated herein by reference for all purposes.

FIELD OF THE INVENTION

The present invention provides a method to treat anemia whereby an alternate dosing regimen is used to raise and maintain hemoglobin levels with dosing intervals greater than one week after the hemoglobin level was elevated with weekly administration.

BACKGROUND OF THE INVENTION

Erythropoietin (EPO) is a glycoprotein hormone secreted by the kidneys in response to tissue hypoxia, which stimulates red blood cell production in the bone marrow (1). The gene for EPO has been cloned and expressed in Chinese hamster ovary cells (2,3). This recombinant human erythropoietin (epoetin alfa, rhEPO) has an amino acid sequence identical to that of human urinary erythropoietin, and the two are indistinguishable on the basis of functional and immunological assays, although differences exist regarding protein glycosylation, affecting in vivo efficacy (4,5).

In clinical trials to date, rhEPO has been evaluated in normal subjects as well as in patients with various anemic conditions (6,7). EPO induces a brisk hematologic response in normal human volunteers, provided that adequate supplies of iron are available to support increased hemoglobin synthesis (8). The majority of trials have investigated the safety and effectiveness of rhEPO in the treatment of chronic renal failure maintained on dialysis and in those not yet on maintenance dialysis. Other indications approved in the US include anemia secondary to chemotherapy treatment in cancer and anemia associated with zidovudine treatment of human immunodeficiency virus infection. Worldwide, EPO has been used to treat anemia associated with rheumatoid arthritis, prematurity, myelofibrosis, sickle cell anemia, bone marrow transplantation, thermal injury, β-thalassemia, as a facilitator of presurgical autologous blood donation, and use as a presurgical adjuvant (6,7). Although rhEPO is generally well tolerated, occasional skin rashes and urticaria have been observed suggesting allergic hypersensitivity to some components of the Epoetin alfa formulation, likely human serum albumin. Further, despite blood screening, there exists a risk of infection with a transmissible agent when a pharmaceutical agent is formulated using human blood products. Therefore pharmaceutical formulations of rhEPO that are stable and are free of human blood products, such as albumin are needed.

Epoetin alfa has been effectively and safely used to raise and maintain target hemoglobin when dosed weekly. Recent efforts have attempted to decrease dosing frequency by increasing the dose level and/or by modifying erythropoietin (EPO) to increase the serum half-life. We sought to address the following questions in a non-human primate model system. 1.) Is a target hemoglobin level achieved faster with a weekly dosing regimen as compared to high dose EPO administration given less frequently? 2.) Is rHuEPO effective at maintaining hemoglobin level with a less frequent dosing interval if initiated at an elevated hemoglobin level? A cohort of cynomolgus primates were dosed weekly, 5000 IU/kg sc until a 3–4 g/dL increase in hemoglobin was achieved. Animals were then randomized into two different EPO dose level groups (17,000 or 25,000 IU/kg) given every two or three weeks. At the time of randomization, a second cohort of primates was dosed with EPO at either 17,000 IU/kg or 25,000 IU/kg administered every two or three weeks. Animals remained in the study for 145 days with CBC analysis performed twice weekly. A 3–4 g/dL rise in hemoglobin was observed after 28 days if EPO was given 5,000 IU/kg weekly while the same increase was observed after 50 days if given every two weeks at either 17,000 or 25,000 IU/kg. However, once the target hemoglobin level was achieved, 3–4 g/dL above baseline, it was maintained within 1 g/dL of the target level if EPO was given every two or three weeks. We conclude that target hemoglobin was achieved faster if dosed with a weekly dosing regimen compared to increasing the dose level given less frequently. Secondly, rHuEPO is effective at maintaining target hemoglobin with a two or three week dosing regimen if initiated at elevated hemoglobin levels. Our results show that an alternate dosing regimen whereby hemoglobin is raised by a weekly dosing regimen then switched to either a once every two weeks or once every three weeks dosing regimen is an effective and safe mechanism that provides both convenience and efficacy to the patient population.

SUMMARY OF THE INVENTION

This study demonstrates that cynomolgus monkeys can be used to model long-term erythropoietin studies. Animals were dosed at various concentrations from 5,000 IU/kg to 25,000 IU/kg with no adverse effects. Moreover, no adverse effects were observed up to 150 days of observation. This study shows that more frequent dosing regimens are more effective at increasing hemoglobin as compared to an increased dose given in an interval longer than one week. Animals initiated with high dosing regimens without a priming period reach a 2–3 g/dL rise in some cases after 60 days. On the other hand, elevated hemoglobin levels can be maintained with a two or three-week dosing regimen with no apparent decrease if initiated at an elevated hemoglobin level. More frequent dosing regimens are more effective at elevating hemoglobin as compared to increasing the dose and/or administering at a two or three week regimen. Dosing regimens whereby EPO is given once every two or three weeks may be an effective regimen to maintain hemoglobin level if started after an elevated hemoglobin level was achieved by weekly administration.

BRIEF DESCRIPTION OF THE DRAWING

As shown in FIG. 4, the hemoglobin rise to target level from the group initiated at a baseline hemoglobin level takes longer than that obtained by a weekly dosing regimen. The 25,000 IU/kg dose maintains a higher plateau hemoglobin level as compared to 17,000 IU/kg.

DETAILED DESCRIPTION

Figure 1:
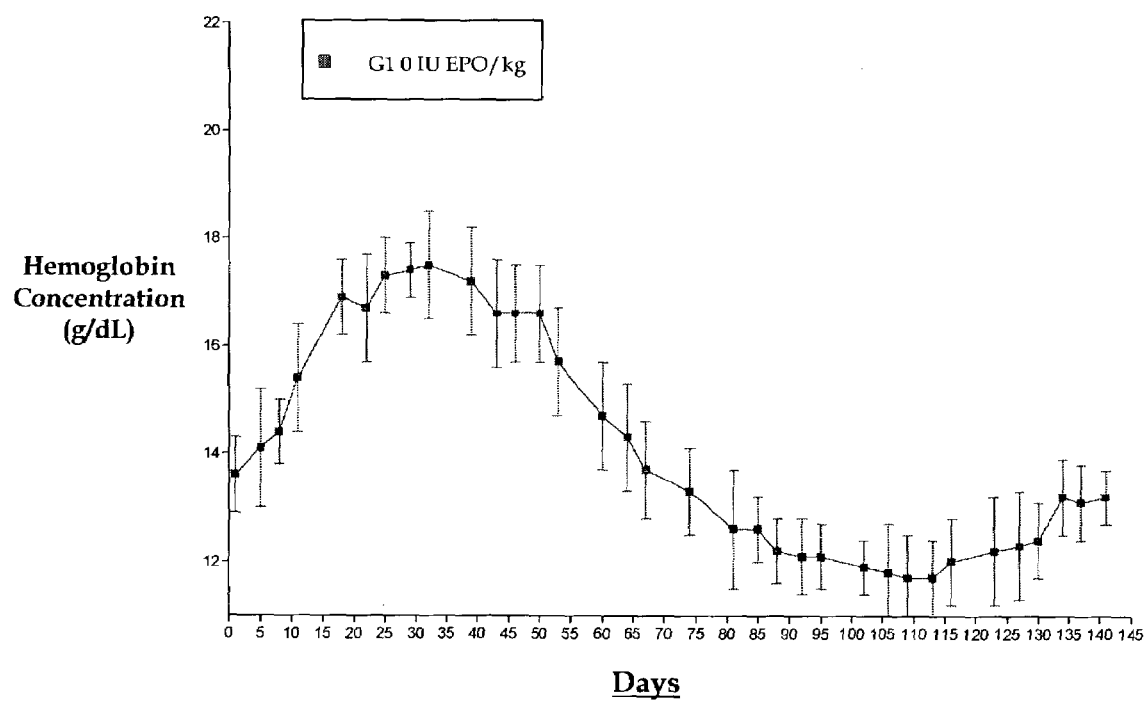
FIG. 1: Six cynomolgus monkeys (*Macaca fascicularis*) were dosed with 5000 IU/kg on Days 1, 8, 15 and 22. Animals remained in study until Day 150. Peripheral blood was collected twice weekly for serum erythropoietin level and hematology analysis. As shown by the graph, a 3–4 g/dL rise in hemoglobin concentration is observed within 28 days. A decline in hemoglobin level is observed post dosing with levels returning to baseline by day 74. No adverse effects were observed up to day 150. This result demonstrates that cynomolgus monkeys can be used to assess the PK/PD parameters of erythropoietin in a long term study.

To characterize the pharmocokinetics/pharmacodynamics of erythropoietin when administered by subcutaneous injections once every two weeks or once every three weeks with or without a priming period in cynomolgus monkeys over a four-month period.

Suitable compositions of erythropoietin for subcutaneous injection include, but are not limited to, those listed in Table A or Table B.

TABLE A

| FORMULA DESCRIPTION | ACTIVE INGREDIENT | INACTIVE INGREDIENTS |
|---|---|---|
| 2000 IU/ml HSA-free | 2000 IU EPO | 4.38 mg Sodium Chloride<br>1.16 mg Sodium phosphate monobasic dihydrate<br>2.23 mg Sodium phosphate dibasic dihydrate<br>5.00 mg Glycine<br>0.30 mg Polysorbate 80<br>Adjust to 1.0 mL with Water for injection |

TABLE A-continued

| FORMULA DESCRIPTION | ACTIVE INGREDIENT | INACTIVE INGREDIENTS |
|---|---|---|
| 40,00 IU/ml HSA-free | 40,00 IU EPO | 4.38 mg Sodium Chloride<br>1.16 mg Sodium phosphate monobasic dihydrate<br>2.23 mg Sodium phosphate dibasic dihydrate<br>5.00 mg Glycine<br>0.30 mg Polysorbate 80<br>Adjust to 1.0 mL with Water for injection |
| 10,000 IU/ml HSA-free | 10,000 IU EPO | 4.38 mg Sodium Chloride<br>1.16 mg Sodium phosphate monobasic dihydrate<br>2.23 mg Sodium phosphate dibasic dihydrate<br>5.00 mg Glycine<br>0.30 mg Polysorbate 80<br>Adjust to 1.0 mL with Water for injection |
| 40,000 IU/mL HSA-free | 40,000 IU EPO | 4.38 mg Sodium Chloride<br>1.16 mg Sodium phosphate monobasic dihydrate<br>2.23 mg Sodium phosphate dibasic dihydrate<br>5.00 mg Glycine<br>0.30 mg Polysorbate 80<br>Adjust to 1.0 mL with Water for injection |

TABLE B

| FORMULA DESCRIPTION | ACTIVE INGREDIENT | INACTIVE INGREDIENTS |
|---|---|---|
| 10,000 multi-dose preserved with cresol | 10,000 IU EPO | 6.25 mg Human serum albumin<br>2.91 mg Sodium phosphate monobasic dihydrate<br>11.19 mg Sodium phosphate dibasic dodecahydrate<br>50.00 mg Glycine<br>7.50 mg m-Cresol<br>Add to 2.5 ml with Water for injection |
| 25,000 multi-dose preserved with cresol | 25,000 IU EPO | 6.25 mg Human serum albumin<br>2.91 mg Sodium phosphate monobasic dihydrate<br>11.19 mg Sodium phosphate dibasic dodecahydrate<br>50.00 mg Glycine<br>7.50 mg m-Cresol<br>Add to 2.5 ml with Water for injection |
| 40,000 multi-dose preserved with cresol | 40,000 IU EPO | 5.00 mg Human serum albumin<br>2.33 mg Sodium phosphate monobasic dihydrate<br>8.95 mg Sodium phosphate dibasic dodecahydrate<br>40.00 mg Glycine<br>6.00 mg m-Cresol<br>Add to 2.0 ml with Water for injection |

The erythropoietin is present in the compositions in therapeutically effective amounts. "Erythropoietin" shall include those proteins that have the biological activity of human erythropoietin, as well as erythropoietin analogs, erythropoietin isoforms, erythropoietin mimetics, erythropoietin fragments, hybrid erythropoietin proteins, fusion proteins oligomers and multimers of the above, homologues of the above, glycosylation pattern variants of the above, and muteins of the above, regardless of the biological activity of same, and further regardless of the method of synthesis or manufacture thereof including but not limited to, recombinant whether produced from cDNA or genomic DNA, synthetic, transgenic, and gene activated methods. Specific examples of erythropoietin include, Epoetin alfa (EPREX®, ERYPO®), Novel erythropoiesis stimulating protein (NESP or darbepoetin) (a hyperglycosylated analog of recombinant human erythropoietin (Epoetin) described in European patent application EP640619), human erythropoietin analog—human serum albumin fusion proteins described in the international patent application WO99/66054, erythropoietin mutants described in the international patent application WO99/38890, erythropoietin omega, which may be produced from an Apa I restriction fragment of the human erythropoietin gene described in U.S. Pat. No. 5,688,679, altered glycosylated human erythropoietin described in the international patent application WO99/11781, PEG conjugated erythropoietin analogs described in WO98/05363 or U.S. Pat. No. 5,643,575. Specific examples of cell lines modified for expression of endogenous human erythropoietin are described in international patent applications WO99/05268 and WO94/12650.

The effect of erythropoietin maybe monitored by measuring the hematocrit with the target hematocrit range being 30 to 33%. Dose adjustment may be made by monitoring the hematocrit. The single use vials of erythropoietin typically contain 2,000, 3,000 4,000 10,000, 40,000, 80,000, 100,000 120,000 or greater units of erythropoietin (1 IU corresponds to about 8.4 nanograms recombinant erythropoietin). As the formulations in one embodiment of the present invention are preserved and provide the benefit of being multi-dose, the formulations preferably will contain a multiple many times the number of units of erythropoietin present in a single-use vial. Compositions containing 1,000 to 120,000 units or more of erythropoietin per vial are included within the present invention. In general it is contemplated that an effective amount will be from about 1 to 500 I.U./kg body weight and more preferably from 50 to 300 I.U./kg body weight especially erythropoietin given subcutaneously. The effective amount will further depend on the species and size of the subject being treated, the particular condition or disease being treated and its severity and the route of administration. In any case the dose to be used should be non-toxic to the host.

The following examples illustrate the present invention without, however, limiting the same thereto.

EXAMPLE 1

Figure 2:
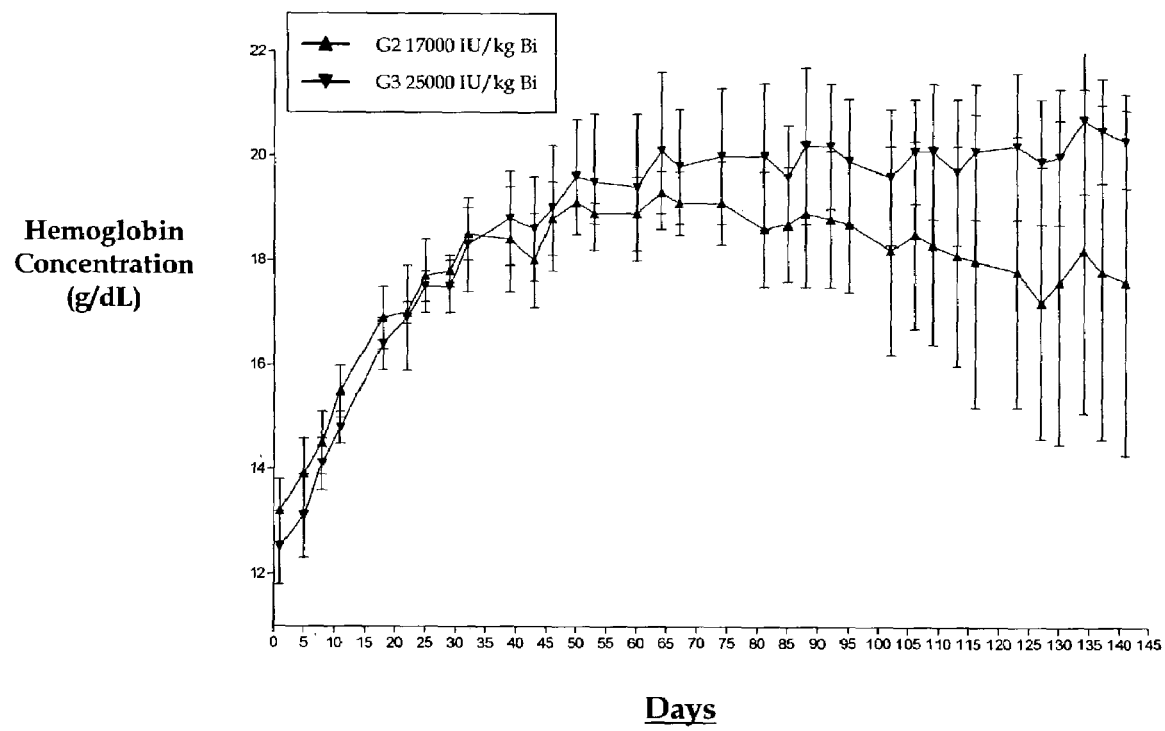
FIG. 2: Two groups of cynomolgus monkeys were dosed weekly (5,000 IU/kg) on Days 1, 8, 15, and 22 to elevate hemoglobin levels 3–4 g/dL above study initiation levels. Animals were then switched to a bi-weekly dosing regimen (Days 29, 43, 57, 71 85, 99, 113, 127 and 141) of 17,000 or 25,000 IU/kg. The hemoglobin level is maintained within 1 g/dL of the level obtained by a weekly dosing regimen. The 30,000 IU/kg dose is able to sustain an elevated hemoglobin more efficiently than that obtained with 15,000 IU/kg.
Figure 3:
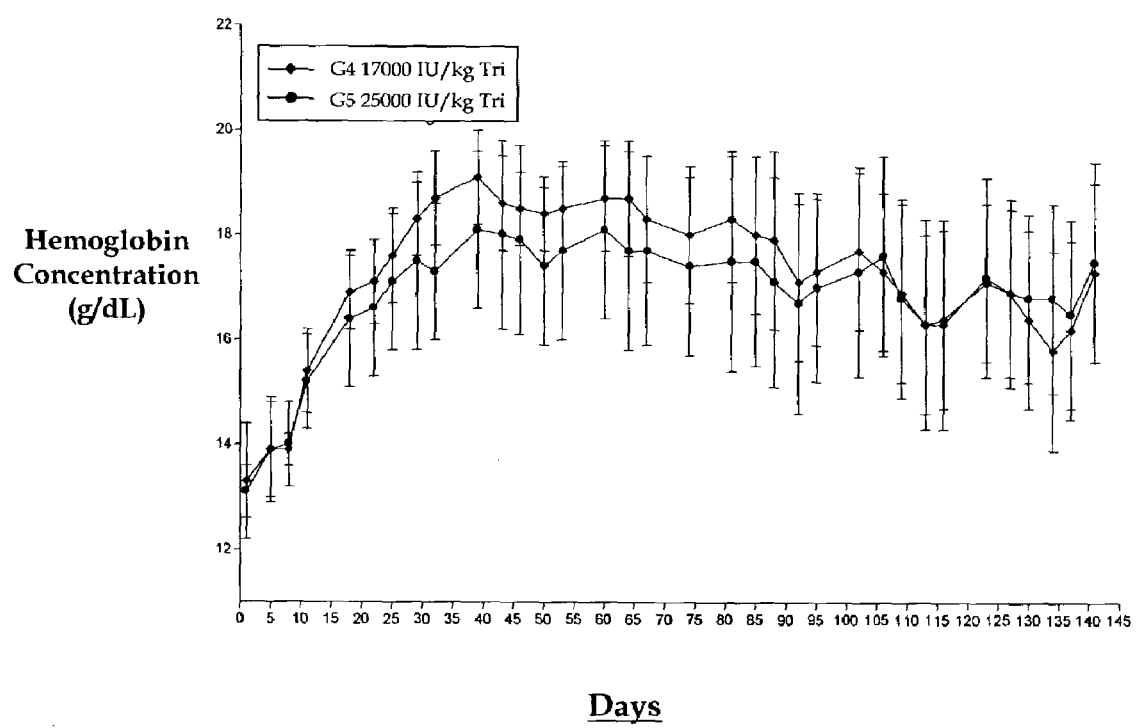
FIG. 3: Two groups of cynomolgus monkeys were dosed weekly (5,000 IU/kg) on Days 1, 8, 15, and 22 to elevate hemoglobin levels 3–4 g/dL above study initiation levels. Animals were then switched to a tri-weekly dosing regimen (Days 29, 50, 71, 92, 113 and 134) of 17,000 or 25,000 IU/kg. The hemoglobin level is maintained within 1 g/dL of the level obtained by a weekly dosing regimen. Although the tri-weekly dosing regimen does not maintain target hemoglobin levels as effectively as the two week dosing regimen, no difference was observed between the 17,000 or 25,000 IU/kg dose.
Figure 4:
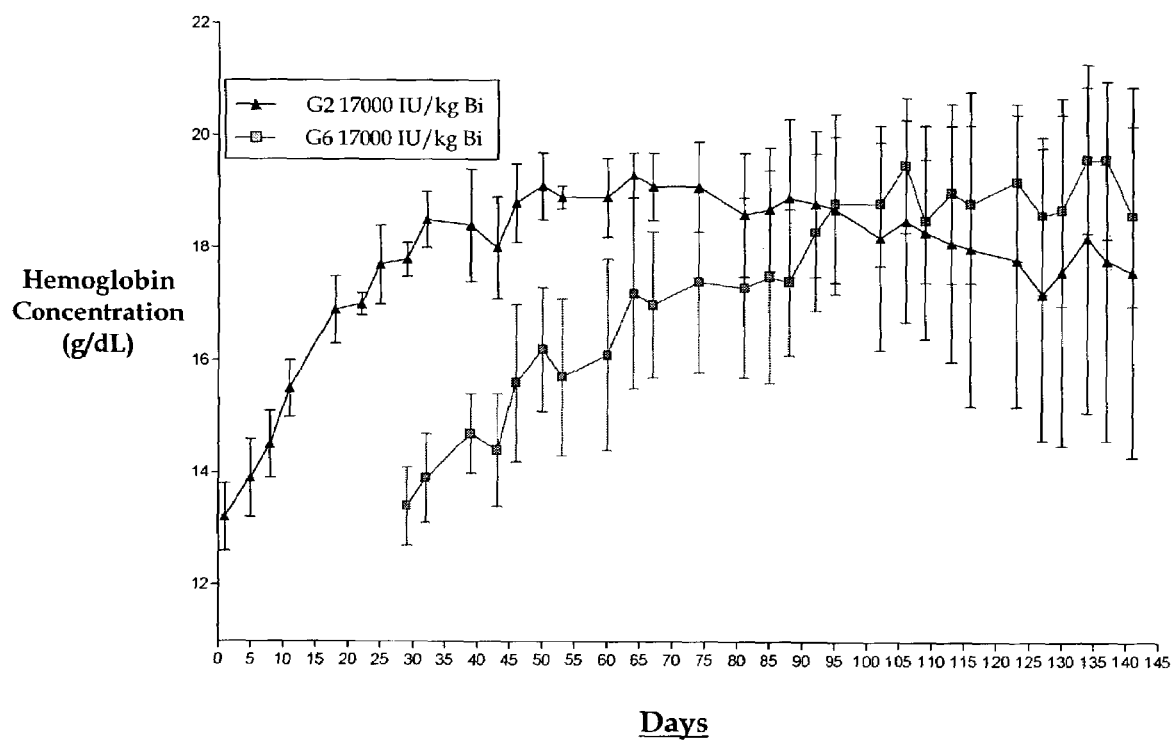
FIG. 4: A group of cynomolgus monkeys were dosed weekly (5,000 IU/kg) on Days 1, 8, 15, and 22 to elevate hemoglobin levels 3–4 g/dL above study initiation levels. Animals were then switched to a biweekly dosing regimen, (Days 29, 43, 57, 71 85, 99, 113, 127 and 141) of 17,000 IU/kg. At Day 29, a second group of animals were initiated into study with a biweekly dosing regimen of 17,000 IU/kg dosed on the days shown above. As shown by the graph, the group that started at a normal hemoglobin level does not intersect the primed group until Day 95. This is ≈66 days post study initiation.
Figure 5:
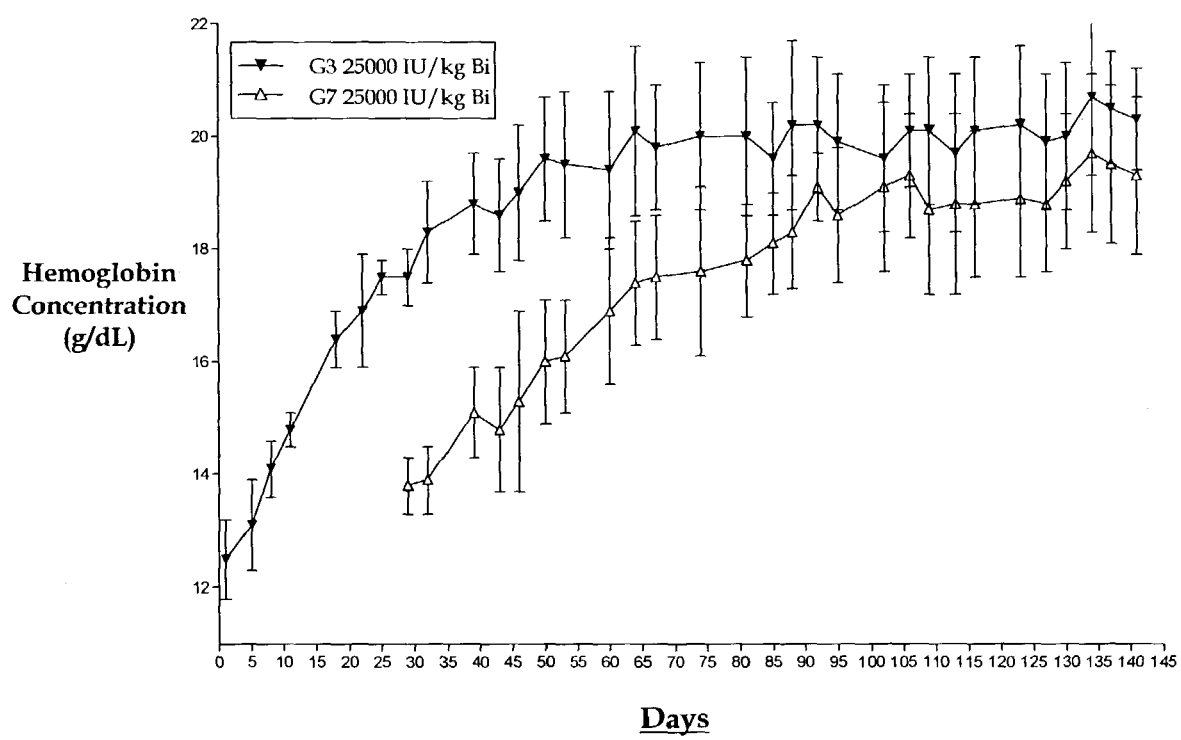
FIG. 5: A group of cynomolgus monkeys were dosed weekly (5,000 IU/kg) on Days 1, 8, 15, and 22 to elevate hemoglobin levels 3–4 g/dL above study initiation levels. Animals were then switched to a biweekly dosing regimen (Days 29, 43, 57, 71 85, 99, 113, 127 and 141) of 25,000 IU/kg. At Day 29, a second group of animals were initiated into study with a biweekly dosing regimen of 25,000 IU/kg dosed on the days shown above.

A non-human primate study was initiated to study biweekly and tri-weekly subcutaneous administration of EPO with or without a series of loading doses evaluated over a four-month period. This study was conceptualized since current dosing regimens administer EPO weekly or three times per week. The goal of this study was to test the hypothesis that if hemoglobin levels are elevated by a series of weekly doses can one then switch to a less frequent dosing regimen. We set out to design a protocol whereby groups of animals were dosed weekly (5000 IU/kg) until a 2 to 4 g/dL rise in hemoglobin was obtained at which point the animals were divided into higher dosing regimens (17,000 or 25,000 IU/kg) given every two or three weeks. The "primed" animal groups were matched with groups dosed at the same higher doses initiated at normal hemoglobin levels. The results are shown in FIGS. 1 through 5.

TABLE C

| GROUP NO. | ANIMAL NO. (MALE/ FEMALE) | TEST ARTICLE | PRIMING DOSE | FREQUENCY | DOSE LEVEL (IU/KG) |
|---|---|---|---|---|---|
| 1 | 3/3 | vehicle | Yes | | 0 (control) |
| 2 | 3/3 | EPO | Yes | Biweekly | 17,000 |
| 3 | 3/3 | EPO | Yes | Biweekly | 25,000 |
| 4 | 3/3 | EPO | Yes | Tri-weekly | 17,000 |
| 5 | 3/3 | EPO | Yes | Tri-weekly | 25,000 |
| 6 | 2/2 | EPO | No | Biweekly | 17,000 |
| 7 | 2/2 | EPO | No | Biweekly | 25,000 |

What is claimed is:

1. A method of raising and maintaining the hemoglobin levels in a patient comprising:
   a) administering an effective amount of about 5,000 IU/kg of erythropoietin to a patient by a subcutaneous injection once every week until a hemoglobin increase of about 2 g/dL is achieved; and
   b) after achieving the hemoglobin increase of step (a), administering, by subcutaneous injection once every two weeks, an amount that is greater than the amount administered in step (a), such that a hemoglobin level within about 1 g/dL of that achieved in step (a) is maintained.

2. The method of claim 1, wherein said erythropoietin administered in step (b) is in an amount of 17,000 to 25,000 IU/kg.

3. The method of claim 1 wherein the patient is treated for anemia secondary to chemotherapy treatment in cancer.

4. The method of claim 1 wherein said erythropoietin is human recombinant erythropoietin.

5. The method of claim 1 wherein said erythropoietin is Epoietin-α.

6. A method of raising and maintaining the hemoglobin levels in a patient comprising:
   a. administering an effective amount of about 5,000 IU/kg of
      erythropoietin to a patient by a subcutaneous injection once every week until a hemoglobin increase of about 2 g/dL is achieved; and
   b. after achieving the hemoglobin increase of step (a), administering, by subcutaneous injection once every three weeks, an amount that is greater than the amount administered in step (a), such that a hemoglobin level within about 1 g/dL of that achieved in step (a) is maintained.

7. The method of claim 1, wherein said erythropoietin administered in step (b) is in an amount of 17,000 to 25,000 IU/kg.

8. The method of claim 6 wherein the patient is treated for anemia secondary to chemotherapy treatment in cancer.

9. The method of claim 6 wherein said erythropoietin is human recombinant erythropoietin.

10. The method of claim 6 wherein said erythropoietin is Epoietin-α.

* * * * *